United States Patent [19]

Naylor

[11] 4,436,672

[45] Mar. 13, 1984

[54] OIL RECOVERY METHOD UTILIZING GLYCERYL ETHER SULFONATES

[75] Inventor: Carter G. Naylor, Austin, Tex.

[73] Assignee: Texaco, Inc., White Plains, N.Y.

[21] Appl. No.: 408,364

[22] Filed: Aug. 16, 1982

[51] Int. Cl.$^3$ .................... C07C 143/42; C07C 143/11
[52] U.S. Cl. ............................ 260/512 R; 260/513 R;
252/8.55 D; 166/274; 166/275
[58] Field of Search .......................... 260/512 R, 513 R

[56] References Cited

U.S. PATENT DOCUMENTS 4,153,575 5/1979 Kalfoglow et al. ............. 260/512 R
4,222,957 9/1980 Watts, Jr. et al. .............. 260/512 R

*Primary Examiner*—Nicky Chan

*Attorney, Agent, or Firm*—Robert A. Kulason; Jack H. Park; Richard A. Morgan

[57] ABSTRACT

Petroleum may be recovered from petroleum containing formations having high salinity and/or high temperature by injecting into the formation an aqueous fluid containing an effective amount of a surface active agent characterized by the formula:

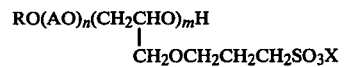

wherein R is an alkyl or alkylaryl radical, AO is an alkylene oxide radical, n is an integer of from 1 to 50, m is an integer from 1 to 10 and X is a sodium, potassium or ammonium cation.

7 Claims, No Drawings

OIL RECOVERY METHOD UTILIZING GLYCERYL ETHER SULFONATES

BACKGROUND OF THE INVENTION

1. Field of the Invention

This invention relates to a novel surfactant water flooding enhanced oil recovery process. The invention also relates to a glyceryl ether sulfonate composition of matter. The invention further relates to solutions containing a glyceryl ether sulfonate. The solutions are useful for recovering petroleum in an enhanced oil recovery process.

2. Prior Art

The crude oil which has accumulated in subterranean reservoirs is recovered or produced through one or more wells drilled into the reservoir. In the initial production, the crude oil is produced by primary recovery techniques wherein only the natural forces present in the reservoir are utilized to produce the oil. However, upon depletion of these natural forces and the termination of primary recovery a large portion of the crude oil remains trapped within the reservoir. Additionally, many reservoirs lack sufficient natural forces to be produced by primary methods from the very beginning. Recognition of these facts has led to the development and use of many enhanced oil recovery techniques. Most of these techniques involve injection of at least one fluid into the reservoir to produce an additional amount of crude oil therefrom. Some of the more common methods are water flooding, steam flooding, immiscible flooding, $CO_2$ flooding, polymer flooding, surfactant flooding, caustic flooding, and in situ combustion.

Water flooding, which involves injection of water into the subterranean oil reservoir for the purpose of displacing the crude oil from the pore spaces of the reservoir rock toward the producing wells, is the most economical and widely used of the enhanced oil recovery methods. Nevertheless, water does not displace oil with high efficiency because of the immiscibility of water and oil and because of the high interfacial tension between them.

Surfactant flooding involves the addition of one or more surface active agents or surfactants to the water flood for the purpose of minimizing the water flooding problems mentioned above. This has been an area of active interest in the art of enhanced oil recovery methods for many years. U.S. Pat. No. 3,302,713 discloses the use of petroleum sulfonates as effective surfactants in oil recovery operations. Other surfactants proposed for use in oil recovery processes include alkyl sulfates, alkyl aryl sulfates, ethoxylated alkyl or alkyl aryl sulfates, alkyl sulfonates, alkyl aryl sulfonates, and quaternary ammonium salts.

One major drawback of most of the above surfactants is the fact that they will precipitate where the water hardness, i.e. the concentration of divalent ions including calcium and magnesium, is relatively high. Since many formations contain very hard water, these surfactants are useless in some applications.

Another problem which frequently detracts from the performance of surfactants is that many degrade chemically and/or in performance at high formation temperatures. Petroleum sulfonates as well as other alkyl or alkylaryl sulfonates are relatively stable at room temperatures and at temperatures encountered in some subterranean petroleum reservoirs. However, these materials are usually not effective in the presence of high salinities and/or high formation water hardness. Conversely, nonionic surfactants such as polyethoxylated alkyl phenols are effective for surfactant flooding in formations containing high salinity water or hard water but these materials become insoluble at temperatures in the range of from about 100° F. to about 125° F. Therefore, if a reservoir is at this temperature, these materials are not effective.

One type of anionic surfactant which is frequently effective for use as a co-surfactant in combination with petroleum sulfonates or alkyl or alkylaryl sulfonates is a water soluble sulfate salt of a polyethoxylated alcohol or alkyl phenol. However, the sulfate linkage is highly sensitive to temperature and hydrolysis or other permanent degradation of the sulfate linkage which take place at high temperatures. For example, the sulfate salt of a polyethoxylated alkyl phenol having an alkyl chain link of about nine carbon atoms and having approximately four or five ethylene oxide groups per molecule is degraded at about 140° F. This is not an unusually high temperature for certain reservoirs and since the surfactant will ordinarily be present in the formation for long periods of time, even years, the thermal stability of the surfactant solution becomes extremely important.

It is an object of this invention to provide surfactants which are tolerant of formation water salinity hardness and which are tolerant of temperatures in excess of 120° F. for long periods of time without hydrolizing or becoming insoluble.

U.S. Pat. Nos. 3,638,728 Hill, 3,653,440 Reisberg and 4,318,816 Schievelbein describe certain organic sulfonates.

SUMMARY OF THE INVENTION

The invention is an oil recovery process for use in subterranean, oil bearing formations whose temperatures are in excess of 120° F. and which may also contain highly saline and/or hard water, e.g. water containing appreciable quantities of sodium chloride and/or water soluble salts of divalent cations such as calcium or magnesium. The process comprises injecting an aqueous surfactant fluid into the subterranean formation and producing oil from production wells in the formation. The surfactants useful in this invention are surface active agents having the general formula:

wherein R is a linear or branched alkyl radical or mono- or polyalkyl substituted benzene radical containing from 8 to 24 carbon atoms, AO is an alkylene oxide radical of from 2 to 4 carbon atoms, n is an integer of from 1 to 50, m is an integer of from 1 to 10 and X is a sodium, potassium or ammonium cation.

These surface active agents may be used as the only constituent in an aqueous solution or they may be used in combination with each other or with an anionic surfactant such as petroleum sulfonate.

DESCRIPTION OF THE PREFERRED EMBODIMENTS

This invention concerns an improved surfactant water flooding petroleum recovery process suitable for use in high salinity formations, e.g., formations containing water or brine whose salinity is from 20,000 to 240,000 parts per million total dissolved solids, which formation brines frequently also contain high concentration of divalent ions such as calcium and magnesium in the range from 1,000 to 20,000 parts per million. The surfactant fluid is ordinarily compounded to have about the same salinity as the formation water, usually in the range from 50% to 100% and preferably from 75% to 100% of the salinity of the water present in the formation. In one embodiment, the present invention relates to a process for recovering petroleum from a subterranean petroleum bearing formation penetrated by an injection well and a production well which comprises:

(A) injecting into the formation via the injection well a drive fluid comprising water having dissolved therein an effective amount of a surface active agent having the general formula:

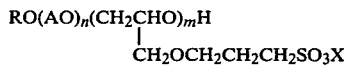

wherein R is a linear or branched alkyl radical or mono- or poly-alkyl substituted benzene radical containing from 8 to 24 and preferably 9 to 20 carbon atoms, AO is an alkylene oxide radical of from 2 to 4 carbon atoms and preferably 2 carbon atoms, n is integer of from 1 to 50 and preferably 2 to 10 and most preferably 3 to 5, m is an integer of from 1 to 10 and preferably 1 to 2 and X is a sodium, potassium or ammonium cation, and (B) forcing the fluid through the formation; and (C) recovering petroleum through the production well.

As previously mentioned, the fluid is typically made up in brine solution and particular compatibility with brine has been found when X is sodium.

The concentration of an effective amount of glyceryl ether sulfonate in aqueous solution will vary depending on the particular homologue chosen from use as well as the water salinity and hardness and the temperature to be encountered in the formation. It is preferred that the optimum response at various concentrations be measured under conditions simulating those which will be present in the formation and the concentration which corresponds to the optimum surfactant performance characteristics be identified in this manner. In actual field use, the concentration of surfactant used will be considerably greater than the optimum value determined from the capillary displacement value in order to compensate for surfactant absorbed by the formation. Generally the concentration of glyceryl ether sulfonate will be from about 0.05 to about 5.0 percent and preferably from about 0.1 to about 2.0 percent by weight.

The volume of surfactant solution to be utilized in the process of this invention can vary from about 2 to about 75 pore volume percent and is preferably from about 10 to about 50 pore volume percent. It is, of course desirable from an economic standpoint to use as small an amount of surfactant as possible to attain the necessary performance.

Ordinarily, the petroleum formation will have been subjected to conventional water flooding before the application of the surfactant solution of this invention; although this is not a requirement for the application of the surfactant process of this invention. Water flooding is generally undertaken if it will result in the recovery of a reasonable quantity of oil above that required by primary means since it is much less costly than surfactant flooding or other means of enhanced recovery. If the surfactant flooding process is to be applied to a formation which has already been water flooded, the water sample tested should be that existing in the formation after water flooding since the concentration of salt as well as water soluble salts of divalent cations such as calcium or magnesium may be changed as a consequence of injecting water differing from the original formation water. As a corollary to this, the formation temperature after water flooding should be ascertained since it may have been altered as a consequence of the water flooding process. Preflushing with a sacrificial agent, e. g., inorganic phosphate, may be useful to minimize adsorption losses of the surfactant on the formation matrix.

It is also common practice to follow the surfactant solution with an aqueous solution which contains little or no surfactant but which has dissolved in it a substance which increases viscosity of the water so as to attain a favorable mobility ratio between that solution and the previously injected surfactant solution. Hydrophilic polymers such as sodium polyacrylamide or polysaccharides are commonly utilized for this purpose. The type and quantity of viscosity increasing polymer injected subsequent to the surfactant solution can generally be the same as in regularly used for such purposes in conventional surfactant flooding. Generally from about 5 to about 50 pore volume percent of an aqueous solution containing from about 100 to about 800 parts per million of the hydrophilic polymer is used. This is followed by water injection which is continued until the water-oil ratio of the fluid being recovered from the formation increases to a point where further injection of water is uneconomical. It is, of course, also acceptable to increase the viscosity of the surfactant fluid by incorporation of a similar polymer.

Another embodiment of the present invention is an aqueous fluid comprising:

(A) about 0.1 wt% to about 2 wt% of a surface active agent of the formula:

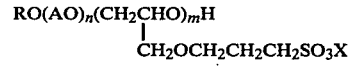

wherein R is a linear or branched alkyl radical or mono- or poly-alkyl substituted benzene radical containing from 8 to 24 and preferably 9 to 20 carbon atoms, AO is an alkylene oxide radical of from 2 to 4 carbon atoms and preferably 2 carbon atoms, n is an integer of from 1 to 50 and preferably 2 to 10 and most preferably 3 to 5, m is an integer of from 1 to 10 and preferably 1 or 2 and X is a sodium, potassium or ammonium cation; and (B) about 0.1 wt% to about 4 wt% of a petroleum sulfonate.

It is preferred that the petroleum sulfonate be at least partially water soluble with an average equivalent weight at a range of from about 350 to 500. The ratio of the glyceryl ether sulfonate to petroleum sulfonate should be from 0.05 to 1 and preferably from 0.1 to 1.0.

The water which makes up the aqueous medium of the fluid mixture of this invention may be either hard of soft. The invention has been found to be particularly useful in hard water such as brine which contains large amounts of divalent ions. That is, the invention is especially effective for stabilizing aqueous surfactant solutions in which the aqueous medium contains large amounts of calcium and/or magnesium ions and is considered hard water. It is in these hard waters that some surfactants are particularly prone to be unstable. It is known in the art that surfactants such as petroleum sulfonates are not at all compatible with calcium and magnesium ions in hard water. Recent discoveries have shown that the sulfonates of alkylene oxide adducts of substituted phenols are compatible with calcium and magnesium ions in hard water or brine but their stability, that is their ability to remain in solution under all conditions of temperature and water hardness and salinity, is at times a problem. Therefore, the invention while including all types of water is particularly directed to hard water brines. Hard water may be defined as an aqueous solution containing from 100–20,000 parts per million polyvalent metal ions such as calcium and/or magnesium ions. Brines contain a minor amount to 25% by weight sodium chloride and many contain various amounts of other dissolved salts such as sodium bicarbonate, sodium sulfate, and sodium borate. The invention is operable in hard water, brines or hard water brines.

The water may also contain dissolved nitrogen, hydrogen sulfide, carbon dioxide, methane or other gases.

The various materials available under the general name of petroleum sulfonates vary in composition according to the petroleum fraction used for sulfonation and in the degree of sulfonation imparted to the petroleum fraction. Preferable petroleum sulfonates prepared from a petroleum fraction whose boiling range is from 700° F. to 1100° F. which corresponds to a molecular weight range of from about 350 to about 500. The sodium salt of the sulfonated product of this petroleum fraction is an excellent material for use in the present invention. The potassium and ammonium salts are also useful.

Mixtures of petroleum sulfonates can also be employed as the sulfonate component of this invention. For example, a mixture of predominantly water soluble petroleum sulfonate having an average equivalent weight of less than 400 and preferably less than 350 may be utilized along with a second petroleum sulfonate which is at least partially oil soluble and having an average equivalent weight of about 400 to about 600 and preferably about 450 to about 550.

It has been found that the degree of solubility of the surfactant composition in the field water is extremely critical to the oil recovery efficiency in the process. If the surfactant is much more soluble in water than oil, then the surfactants tends to be distributed throughout the bulk of the water phase including both formation water and injected drive water, and little effectiveness will be achieved at the interfacial zones between oil and water. Similarly, if the surfactant is substantially more soluble in oil than it is in water, the surfactant will partition into and distribute itself throughout the oil phase, and will have little effect on the surface tension existing at the interfacial zone between oil and water. The optimum surfactant effectiveness is achieved if there is a condition of borderline solubility of the surfactant fluid in the drive water and/or formation water, so the surfactants tend to exist in higher concentrations at the interfacial zone between oil and water than in either the oil phase or the water phase.

It has been found that when using blends of petroleum sulfonates and the glyceryl ether sulfonate of the present invention, optimum oil recovery efficiency occurs when the concentrations of the materials are carefully balanced so as to produce a condition of borderline solubility. If too little solubilizing cosurfactant is used, the primary surfactants are rendered insoluble and at least a portion thereof will precipitate in the aqueous solution. This can, as discussed above, result in at least reducing the effectiveness of the surfactant fluid for the purpose of recovering oil, and may lead to permanent, irreversible damage to permeability of the formation matrix, which will prevent any further displacement of petroleum from the formation. On the other hand, if more than the minimum amount of solubilizing glyceryl ether sulfonate which achieves the conditions described above as borderline solubility is used in combination with petroleum sulfonate, the surfactants are rendered too soluble in the aqueous phase and the amount of oil displaced by such a solution being injected into a formation is reduced fairly substantially. Moreover, since the cost of the glyceryl ether sulfonate is high compared to that of petroleum sulfonate, the result of using too much solubilizing glyceryl ether sulfonate is to increase the fluid cost and the amount of oil recovered by the use of the fluid is decreased, with rapidly diminishing economic attractiveness of the process.

The amount of solubilizing glyceryl ether sulfonate to achieve the above described desired condition of borderline solubility is highly dependent on all of the possible variations in the structural characteristics of the surfactant molecules employed. The average equivalent weight of the petroleum sulfonate for example, will affect the amount of glyceryl ether sulfonate required to achieve the condition of borderline solubility. For example, any change in the length of the alkyl chain which comprises the hydrophobe of the surfactant molecule, or a change in the number of alkylene oxide groups condensed with the molecule, will change the amount of glyceryl ether sulfate cosurfactant needed to achieve the condition of borderline solubility with whatever primary anionic surfactant or mixture thereof it is used. Furthermore, the aqueous fluid salinity and the concentration of divalent ions present in the fluid will also vary the amount of the surfactants needed to achieve borderline solubility. Generally, higher salinity and/or higher concentrations of divalent ions of the aqueous fluid in which the surfactants are dissolved require increasing number of alkylene oxide units to be present on the solubilizing cosurfactant molecule.

It has been found that one satisfactory method for determining the proper concentrations of petroleum sulfonate and glyceryl ether sulfonate is found in U.S. Pat. No. 4,066,124 which is incorporated herein in its entirety by reference. By this method it has been found that brine solutions of about 0.1 wt% to about 2 wt% of the glyceryl ether propane sulfonate of the present invention and about 0.1 wt% to about 4 wt% of a petroleum sulfonate herein defined produce advantageous results in an enhanced oil recovery process. These advantageous results include applications where hydrolytically and thermally stable surface active agents soluble in salt solutions containing divalent cations. Advantageous results are also achieved where relatively viscous solutions or emulsions are desired.

The fluids of the present invention are typically solutions, but can be micellar dispersions as well.

One unexpected advantage of the glyceryl ether sulfonate of the present invention is the surprising stability and viscosity displayed by some of the compounds over a wide range of salinities and temperatures. Another advantage is that the glyceryl ether sulfonates of the present invention are more efficient than monosulfonates made from the same hydrophobes, and therefore less solubilizing cosurfactant is required for a given amount of petroleum sulfonate.

In another embodiment, the present invention relates to a composition of matter characterized by the formula:

$$RO(AO)_n(CH_2\underset{|}{C}HO)_mH$$
$$CH_2OCH_2CH_2CH_2SO_3X$$

where R is a linear or branched alkyl radical or mono- or poly-alkyl substituted benzene radical containing from 8 to 24 and preferably 9 to 20 carbon atoms, AO is an alkylene oxide radical of from 2 to 4 carbon atoms, n is an integer of from 1 to 50 and preferably 2 to 10 and most preferably 3 to 5, m is an integer of from 1 to 10 and preferably 1 or 2 and X is a sodium, potassium or ammonium cation. Sodium is a preferred cation.

Compounds of the present invention are prepared in a unique sequence.

(1) Preparation of alkylene oxide adduct - Alkoxylation

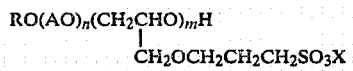

ROH + CH$_2$CH ———➤ RO(AO)$_n$H (2) Addition of allyl glycidyl ether - Etherification

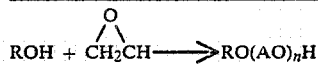

RO(AO)$_n$H + mCH$_2$CHCH$_2$OCH$_2$CH=CH$_2$ ——➤

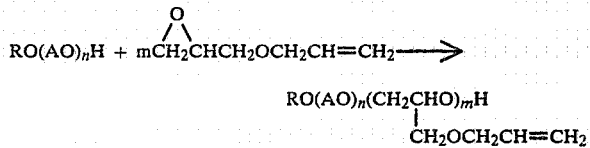

RO(AO)$_n$(CH$_2$CHO)$_m$H
           |
           CH$_2$OCH$_2$CH=CH$_2$ (3) Bisulfite addition - Sulfonation RO(AO)$_n$(CH$_2$CHO)$_m$H             + XHSO$_3$ ——➤
           |
           CH$_2$OCH$_2$CH=CH$_2$

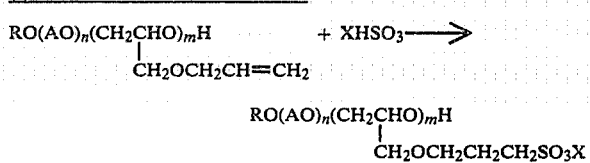

RO(AO)$_n$(CH$_2$CHO)$_m$H
           |
           CH$_2$OCH$_2$CH$_2$CH$_2$SO$_3$X

This synthesis of glyceryl ether sulfonates provides a method of producing the ether sulfonates which avoids chlorine containing alkylating agents and inorganic chlorine. This offers significant processing, health and safety advantages.

The synthesis of the composition of the present invention is better shown by way of example.

In the Examples, the degree of alkoxylation can be evaluated by hydroxyl number and epoxide number. Hydroxyl number determinations are well known and used in the art. In the determination, the ether product is reacted with a known quantity of acetic anhydride to change hydroxyl groups to acetate groups, quantitatively freeing acetic acid. Free acetic acid is determined by titration and from this hydroxyl number is calculated and the concentration of hydroxyl groups in solution.

Epoxide number is determined by titration with HBr.

EXAMPLE I

A commercially available 5-molar ethoxylated nonylphenol (500 grams, 1.1 moles) and 1 gram of sodium metal were mixed in a one liter stirred autoclave with 140 grams (1.1 equivalent) allyl glycidyl ether and heated for one hour at 110° C., two hours at 120° C. and two hours at 150° C. The product had a hydroxyl value of 108 milligrams and no detectable epoxide value.

The product was recovered and 200 grams was dissolved in 200 grams of isopropyl alcohol and 300 grams of water. The solution was buffered at pH 7.2 with sodium hydroxide and sodium bisulfite, heated to 55° C. and purged with air at a rate of 30 ml/min. Aqueous sodium bisulfite was added at a rate to maintain the pH at 7.2 over two hours. After distillation of the alcohol cosolvent and dilution with water, 1067 grams of a clear foamy solution was obtained. The solution contained 0.204 milliequivalents/gram (13.6 wt %) of the anionic surfactant and 6.2 wt % unreacted ether.

This product was extracted three times with ethyl acetate to remove the unreacted fraction. HPLC, high pressure liquid chromatography, analysis of the extracted product gave 51 area % monosulfonate, 23 area % disulfonate, 5 area % higher sulfonates and 21 area % unknowns. Analysis for original 5 molar ethoxylated nonylphenol showed only 0.5 wt % (based on molecular weight of monosulfonate) and 13.3 wt % of the 5 molar ethoxylated nonylphenol glyceryl ether propane sulfonate.

EXAMPLE II

By the method of Example I, a commercially available 3 molar ethoxylated nonylphenol was converted to the glyceryl ether propane sulfonate derivate. Analysis revealed 17.8 wt % active anionic sulfonate and 0.4 wt % nonionic starting material (3-molar ethoxylated nonylphenol). HPLC analysis indicated 56 area % monosulfonate, 24 area % disulfonate, 7 area % high sulfonates and 13 area % unknowns.

EXAMPLE III

The 6.6-molar ethoxylate of technical grade dodecylphenol was converted to glyceryl ether propane sulfonate by the procedure of Example I. The glyceryl ether propane sulfonate product contained 15.8 wt % active and 0.1 wt % nonionic constituents. HPLC analysis indicated 50 area % monosulfonate, 25 area % disulfonate, 8 area % higher sulfonates and 17 area % unknowns.

EXAMPLE IV

The commercially available 3.4-molar ethoxylate of dinonylphenol was treated with 2.0 equivalents of allyl glycidyl ether and sulfonated by the method of Example I. The product contained 15 wt % active and 1.9 wt % nonionic constituents. HPLC analysis indicated 34 area % monosulfonate, 29 area % disulfonate, 15 area % higher sulfonates and 22 area % unknowns.

EXAMPLE V

The 5-molar ethoxylate of nonylphenol was treated with 2.0 equivalents of allyl glycidyl ether and converted to glyceryl ether propane sulfonate by the method of Example I. The product was not extracted. Activity was 21.3 wt % (based on molecular weight of the disulfonate) and 2.2 wt % nonionics. HPLC analysis indicated 41 area % monosulfonate, 31 area % disulfonate, 14 area % higher sulfonates and 16 area % unknowns.

EXAMPLE VI

A synthetic brine concentrate simulating the connate water of the Slaughter field was prepared from: 161 grams NaCl, 41.5 grams CaCl$_2$, 34.7 grams MgCl$_2$.6H$_2$O, 1.0 grams Na$_2$SO$_4$ and 0.3 grams NaHCO$_3$ per liter of solution.

Solutions were made of petroleum sulfonates and the products of Examples I to V in the synthetic brine and tested for temperature solubility limit (cloud point) and appearance. The petroleum sulfonate used was a 70:30 blend of Witco Chemical Company's TRS-40 (equivalent weight 337) and TRS-18 (equivalent weight 502). TRS-40 is an oil soluble petroleum sulfonate and TRS-18 was water soluble. The solution was formulated with 4.3 grams of brine concentrate per 10 grams of solution, giving a brine concentration of 9.46 wt % total dissolved solids, 0.59 wt % calcium and 0.19 wt % magnesium.

The term "cloud point" is recognized in the art as a measure of the relative hydrophilic properties of detergent compounds and is the temperature at which turbidity appears in a 1% aqueous detergent solution when the solution is heated from a cooler temperature to a temperature at which turbidity appears in the solution. Cloud points were measured by heating the solutions until they just clouded (turned opaque to transmitted light), then slowly cooled until the solutions became transparent.

All the solutions were pearlescent below the cloud point, visual evidence of low surface tension, a necessary property for oil displacement from porous rock.

Tables 1, 2 and 3 demonstrates the efficiency of the ether sulfonates of the present invention in solubilizing petroleum solfonates compared to known reference ether sulfonates. N-50 is the 5-molar ethoxylate of nonylphenol. N-30 is the 3-molar ethoxylate of nonylphenol. DNP-34 is the 3.4-molar ethoxylate of dinonylphenol.

As seen from Table 1, 2 and 3 the three reference propane sulfonates were much less effective in solubilizing petroleum sulfonate.

As seen in Table 1, the products of both Example I and Example V were both about 65% more efficient than N-50 propane sulfonate (nonylphenol 5-molar ethoxy propane sulfonate).

As seen in Table 2, the product of Example II was still more efficient while N-30 propane sulfonate (nonylphenol 3-molar ethoxy propane sulfonate) was unable to solubilize even its own weight of the petroleum sulfonate.

Table 3 shows that DNP-34 petroleum sulfonate (nonylphenol 3.4 molar ethoxy propane sulfonate) was insoluble in brine, in contrast to the high efficiency of the product of Example IV. The product of Example III was similar in performance to the product of Example V.

TAVBLE 1

| Solubilizer | Wt % Active | Wt % TRS | TRS/Active Wt %/WT % | Cloud Pt. | Pearlescent |
|---|---|---|---|---|---|
| EX. I | 0.5 | 2.0 | 4/1 | 80° C. | Yes |
|  | 0.5 | 2.5 | 5/1 | 60° C. | Yes |
|  | 0.4 | 2.0 | 5/1 | 63° C. | Yes |
|  | 0.3 | 2.0 | 6.7/1 | 42° C. | Yes |
| EX. V | 0.5 | 2.5 | 5/1 | 58° C. | Yes |
|  | 0.4 | 2.0 | 5/1 | 59° C. | Yes |
|  | 0.3 | 2.0 | 6.7/1 | 45° C. | Yes |
| N-50 Propane Sulfonate | 0.5 | 1.5 | 3/1 | 75° C. | Yes |
|  | 0.5 | 2.0 | 4/1 | 45° C. | Yes |
|  | 0.4 | 2.0 | 5/1 | 30° C. | Yes |

TABLE 2

| Solubilizer | Wt % Active | Wt % TRS | TRS/Active | Cloud Pt. | Pearlescent |
|---|---|---|---|---|---|
| EX. II | 0.5 | 2.0 | 4/1 | 94° C. | Yes |
|  | 0.5 | 3.0 | 6/1 | 60° C. | Yes |
|  | 0.4 | 2.0 | 5/1 | 85° C. | Yes . |
|  | 0.3 | 2.0 | 6.7/1 | 67° C. | Yes |
|  | 0.25 | 2.0 | 8/1 | 54° C. | Yes |
| N-30 Propane Sulfonate | 1.0 | 1.0 | 1/1 | less than 25° C. | No |

TABLE 3

| Solubilizer | Wt % Active | Wt % TRS | TRS/Active | Cloud Pt. | Pearlescent |
|---|---|---|---|---|---|
| EX. III | 0.5 | 2.0 | 4/1 | 72° C. | Yes |
|  | 0.5 | 2.5 | 5/1 | 55° C. | Yes |
| EX. IV | 0.5 | 2.0 | 4/1 | 76° C. | Yes |
|  | 0.5 | 2.5 | 5/1 | 70° C. | Yes |
|  | 0.5 | 3.0 | 6/1 | 65° C. | Yes |
|  | 0.4 | 2.0 | 5/1 | 63° C. | Yes |
|  | 0.3 | 2.0 | 6.7/1 | less than 25° C. | No |
| DNP-34 Propane Sulfonate | 1.0 | 0 | 0/1 | insol. at 25° C. | No. |

EXAMPLE VI

In a field in which the primary production has already been exhausted, an injection well is completed in the hydrocarbon-bearing formation and perforations are formed between the interval of 6890–6910 feet. A production well is drilled approximately 415 feet distance from the injection well, and perforations are similarly made in the same hydrocarbon-bearing formation at (6895–6915) feet.

The hydrocarbon-bearing formation in both the injection well and the production well is hydraulically fractured using conventional techniques, and a gravel-sand mixture is injected into the fracture to hold it open and prevent healing of the fracture.

In the next step, oil field brine of 1000 ppm at a temperature of 75° F. containing dissolved therein 1% by weight petroleum sulfonate and 0.5% by weight of the product of Example I is injected via the injection well into the formation at a pressure of about 1300 psig and at the rate of 1.05 barrels per minute. Injection of the driving fluid continues at the rate of 1.05 barrels per minute and at the end of 67 days, a substantial production of petroleum is achieved.

The principle of this invention and the best mode contemplated for applying that principle have been described. It is to be understood that the foregoing is illustrative only and that other means and techniques can be employed without departing from the true scope of the invention defined in the following claims.

What is claimed is:

1. A composition of matter of the formula:

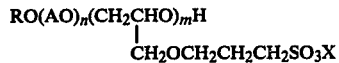

wherein

R is a linear or branched alkyl radical or mono- or polyalkyl substituted benzene radical containing from 8 to 24 carbon atoms; AO is an alkylene oxide radical of from 2 to 4 carbon atoms; n is an integer of from 1 to 50; m is an integer of from 1 to 10; and X is a sodium, potassium or ammonium cation.

2. The composition of matter of claim 1 wherein R is a mono-alkyl substituted benzene radical containing from 9 to 20 carbon atoms.

3. The composition of matter of claim 1 wherein m is an integer of from 1 to 2.

4. The composition of matter of claim 1 wherein AO is an ethoxy radical.

5. The composition of matter of claim 1 wherein n is an integer of 2 to 10.

6. The composition of matter of claim 1 wherein n is an integer of from 3 to 5.

7. The composition of matter of claim 1 wherein X is a sodium cation.

* * * * *